Feb. 3, 1959 R. L. BYRUM Plant Pat. 1,807
ROSE PLANT
Filed June 25, 1958
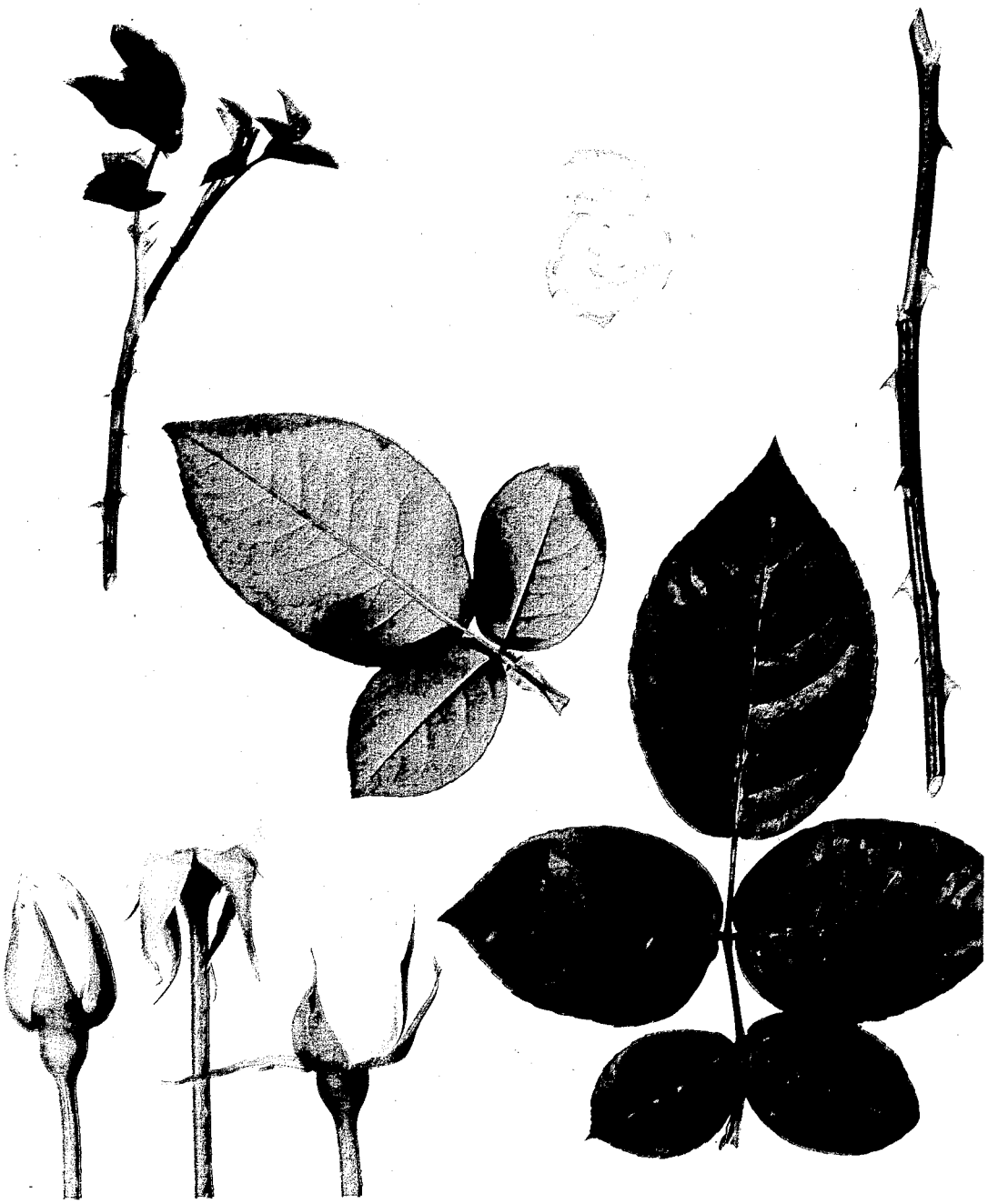
INVENTOR
R. L. Byrum
BY Robbins Cobb
ATTORNEYS United States Patent Office Plant Pat. 1,807
Patented Feb. 3, 1959

1,807

ROSE PLANT

Roy L. Byrum, Richmond, Ind., assignor to Joseph H. Hill Company, Richmond, Ind., a corporation of Indiana Application June 25, 1958, Serial No. 744,627

1 Claim. (Cl. 47—61)

The present invention relates to a new and distinct variety of rose plant of the hybrid tea class, which was originated by me by crossing the variety "Peace" (Plant Patent No. 591) with the variety "Yellow Perfection" (Plant Patent No. 1,083).

The parent variety "Peace" is a well-known and extremely popular garden rose, but it will not "stretch" sufficiently to produce cut flowers of a suitable length, and hence, is not satisfactory or profitable for the commercial production of cut flowers grown under glass. Accordingly, it was the primary objective of this breeding to produce a new rose variety which bears blooms of a color comparable to the blooms of "Peace," but which is more suitable for cut flower forcing than either of the aforementioned parent varieties. It was a further objective to attain a new rose variety of the type noted above, but which produces buds of a longer form than the normal buds of "Peace," and also greater flower petalage than that of the parent variety "Yellow Perfection." These objectives were fully achieved, along with other improvements, as evidenced by the following unique combination of features which are outstanding in the new variety and which distinguish it from its parents, as well as from all other varieties of which I am aware:

(1) A more glossy foliage than that of "Yellow Perfection";

(2) Longer buds than those of "Peace";

(3) A habit of bearing flowers on strong stems of a length suitable for cut flowers;

(4) Greater flower petalage than that of "Yellow Perfection"; and (5) A general color tonality of the flowers which may be best described as solid Straw Yellow in the newly-opened flowers, changing to Naples Yellow as the flowers age, without any red or pink coloration except in the tight bud stage, and with no appreciable change in the flower color during different seasons.

Asexual reproduction of my new variety by grafting, as performed at Richmond, Indiana, and also by budding, as performed at West Grove, Pennsylvania, shows that the aforementioned characteristics and distinctions come true to form and are established and transmitted through succeeding propagations.

The accompanying drawing shows typical specimens of the vegetative growth and flowers of the new variety in different stages of development and is depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson"), Ridgway's Color Standards and Nomenclature (hereinafter abbreviated as "Ridgway"), and Koster's Color Guide (hereinafter abbreviated as "Koster"), as indicated:

Type: Greenhouse; bush; seedling.
Class: Hybrid tea.
Breeding: Seedling.
*Seed parent.*—"Peace."
*Pollen parent.*—"Yellow Perfection."

Propagation: Holds its distinguishing characteristics through succeeding propagations by both grafting and budding.

*Flower*

Locality where grown and observed: Richmond, Indiana.
Flowers borne: One to stem; on long, strong stems.
Quantity of bloom: Free, in greenhouse.
Continuity: Continuous.
Fragrance: Moderate. Nature—tea.
Bud:
*Peduncle.*—Medium length; large; strong; erect. Bark—almost smooth; color—Lettuce Green, Plate 861 (Wilson). Thorns—numerous; color—Chartreuse Green, Plate 663/3 (Wilson). Prickles—numerous; color—Chartreuse Green, Plate 663/3 (Wilson). Hairs—none.
*Before calyx breaks.*—Size—large. Form—short pointed; ovoid; with a conspicuous neck; with foliaceous appendages on the surface of the bud; with foliaceous parts extending beyond the tip of the bud equal to ¼ or more of its length. Color—from Scheeles Green, Plate 860/1 (Wilson) to Scheeles Green, Plate 860 (Wilson).
*As calyx breaks.*—Color—outside of petal—Maize Yellow, Plate 607 (Wilson).
*As first petal opens.*—Size—large. Form—ovoid. Color: outside—Chrome Yellow, Plate 605 (Wilson); inside—Buttercup Yellow, Plate 5/1 (Wilson).
*Opening.*—Opens up well in greenhouse; no unusual characteristics attributed to weather conditions.
Bloom:
*Size (when fully open).*—Very large; from 5 to 6 inches.
*Petalage.*—Double; from 30 to 35 petals; arranged regularly.
*Form.*—Full and high-centered at first, but becoming open; petals at first being tightly rolled outward, but later becoming loosely rolled outward at maturity.
Petals:
*Texture.*—Thick; leathery. Inside—satiny. Outside—satiny.
*Shape.*—Outside petals—obovate, with apex obtuse. Intermediate petals—obovate, with apex obtuse. Inside petals—lanceolate, with apex acute.

This description of a newly opened flower was made from a rose grown in a greenhouse in the month of May, at Richmond, Indiana:

*Color.*—Outer petals: outside surface—Straw Yellow, Plate 604 (Wilson); inside surface—Aureolin, Plate 3/1 (Wilson). Intermediate petals: outside surface—Straw Yellow, Plate 604 (Wilson); inside surface—Aureolin, Plate 3/1 (Wilson). Inner petals: outside surface—Straw Yellow, Plate 604 (Wilson); inside surface—Aureolin, Plate 3 (Wilson).

This description was made from a rose that was open for 3 days in a greenhouse in the month of June, at Richmond, Indiana:

*Color.*—Outer petals: outside surface—Mimosa Yellow, Plate 602/3 (Wilson) at the top of the petal, gradually changing through Mimosa Yellow, Plate 602/2 (Wilson) to Mimosa Yellow, Plate 602/1 (Wilson) at base of petal; inside surface—Mimosa Yellow, Plate 602/3 (Wilson) at the top of the petal, gradually changing through Mimosa Yellow, Plate 602/2 (Wilson) to Mimosa Yellow, Plate 602/1 (Wilson) at base of petal. Intermediate petals: outside surface—Mimosa Yellow, Plate 602/3 (Wilson) at the top of the petal, gradually changing through Mimosa Yellow, Plate 602/2 (Wilson) to Mimosa Yellow, Plate 602/1 (Wilson) at base of petal; inside surface—Mimosa Yellow, Plate 602/3 (Wilson) at the top of the petal, gradually changing through Mimosa Yellow, Plate 602/2 (Wilson) to Mimosa Yellow, Plate 602/1 (Wilson) at base of petal. Inner petals: outside surface—Mimosa Yellow, Plate 602/3 (Wilson) at the top of the petal, gradually changing through Mimosa Yellow, Plate 602/2 (Wilson) to Mimosa Yellow, Plate 602/1 (Wilson) at base of petal; inside surface—Mimosa Yellow, Plate 602/3 (Wilson) at the top of the petal, gradually changing through Mimosa Yellow, Plate 602/2 (Wilson) to Mimosa Yellow, Plate 602/1 (Wilson) at base of petal.

*General color effect.*—Newly opened flower—from Straw Yellow, Plate 604/1 (Wilson) to Straw Yellow, Plate 604 (Wilson). 3-days open—from Naples Yellow, Plate 403/1 (Wilson) to Naples Yellow, Plate 403 (Wilson).

*Behavior.*—Persist.

*Flower longevity.*—Cut roses grown in greenhouse and kept at living-room temperatures—from 4 to 6 days in November.

*Reproductive organs*

Stamens: Many; arranged regularly about pistils.

Filaments: Long; most with anthers. Color—Straw Yellow, Plate 604 (Wilson).

Anthers: Medium large; all open at once. Color—Chrome Yellow, Plate 605 (Wilson).

Pollen: Abundant. Color—Chrome Yellow, Plate 605/3 (Wilson).

Pistils: Many.

Styles: Uneven; medium length; moderately thin; bunched. Color—from Rose Madder, Plate 23/2 (Wilson) to Rose Madder, Plate 23/1 (Wilson).

Stigma: color—from Chinese Yellow, Plate 606/3 (Wilson) to Chinese Yellow, Plate 606/2 (Wilson).

Ovularies: Some protruding from calyx.

Hips: None developed.

Sepals: Permanent; medium length; straight. Color: inside—Scheeles Green, Plate 860/3 (Wilson), overlaid with white fuzz; outside—Scheeles Green, Plate 860/2 (Wilson).

Seeds: None developed.

*Plant*

Foliage:

*Leaves.*—Compound of 3–7 leaflets; abundant; large; moderately thin; glossy; wrinkled.

*Leaflets.*—Shape—ovoid. Apex—acute. Base—round. Margin—simply serrate.

*Color.*—Mature: upper surface—near Spinach Green, Plate 0960 (Wilson); under surface—Bice Green, Plate XVII (Ridgway). Young: upper surface—near Lettuce Green, Plate #74 (Koster), overlaid with near Oxblood Red, Plate 00823/3 (Wilson); under surface—near Oxblood Red, Plate 00823/3 (Wilson).

*Rachis (the supporting stem of the compound leaf).*—Heavy. Upper side—grooved. Under side—smooth.

*Stipules.*—Long; narrow; with short points turning out at an angle of more than 45°.

Growth:

*Habit.*—Bush; upright, much-branched.

*Growth.*—Vigorous.

*Canes.*—Large.

*Main stems.*—Color—some are Spinach Green, Plate 0960 (Wilson), overlaid with Tobacco Brown, Plate #88 (Koster). Thorns—several; medium length; hooked downward; with long, narrow base; color—Fawn, Plate #89 (Koster). Prickles—few; color—Fawn, Plate #89 (Koster). Hairs—none.

*Branches.*—Color—from Spinach Green, Plate 0960/2 (Wilson) to Spinach Green, Plate 0960/1 (Wilson), with some overlaid with Dark Violet, Plate #58 (Koster). Thorns—several; medium length; hooked downward; with long, narrow base; color—Light Yellowish Olive, Plate XXX (Ridgway), with some overlaid with Dark Violet, Plate #58 (Koster). Prickles—none. Hairs—none.

*New shoots.*—Color—near Oxblood Red, Plate 00823/3 (Wilson). Thorns—several; medium length; hooked downward; with long, narrow base; color—near Oxblood Red, Plate 00823/3 (Wilson). Prickles—few; color—near Oxblood Red, Plate 00823/3 (Wilson). Hairs—none.

I claim:

A new and distinct variety of rose plant of the hybrid tea class, substantially as herein shown and described, characterized particularly as to novelty by the unique combination of glossy foliage, long buds, a habit of bearing the flowers on strong stems of a length suitable for cut flowers, good flower petalage, and a distinctive flower general color tonality of solid Straw Yellow in the newly-opened flowers, changing to Naples Yellow as the flowers age, without any red or pink coloration except in the tight bud stage, and with no appreciable change in the flower color during different seasons.

No references cited.